United States Patent [19]

Carrier et al.

[11] Patent Number: Plant 7,649

[45] Date of Patent: Sep. 10, 1991

[54] ALSTROEMERIA NAMED VICIA

[75] Inventors: Leonard E. Carrier, Encinitas, Calif.; Stephen Garton, West Jordan, Utah

[73] Assignee: Native Plants, Inc., Salt Lake City, Utah

[21] Appl. No.: 512,811

[22] Filed: Apr. 20, 1990

[51] Int. Cl.[5] ..... A01H 5/00
[52] U.S. Cl. ..... Plt./68
[58] Field of Search ..... Plt./68

*Primary Examiner*—Howard J. Locker

*Attorney, Agent, or Firm*—Venable, Baetjer, Howard & Civiletti

[57] ABSTRACT

This plant is particularly characterized by its dwarf habit which makes the plant eminently suitable for cultivation as a potted plant. In addition, the plant bears several flowering stalks which carry large attractive flowers which are predominantly of a deep pink coloration. The attractive flowers and desirable growth habit of this plant provide a novel addition to the range of Alstroemerias.

1 Drawing Sheet

BACKGROUND OF THE NEW PLANT

This new variety of Alstroemeria originated as a seedling resulting from crossing two plants growing among a collection of breeding stock maintained in a greenhouse in Encinitas, Calif. The seedling was selected for further propagation and testing because of the dwarf characteristic of the whole plant, and the attractive color of the many large flowers contained in several inflorescences as the plant bloomed in a pot. The select plant was propagated in Salt Lake City, Utah by division of the rhizomatous rootstock and through tissue culture. The distinguishing characteristics of the new plant hold true in successive vegetative generations and appear to be firmly fixed. Propagation work is currently being carried out in Salt Lake City using tissue culture methods.

DESCRIPTION OF THE DRAWING

This new variety of Alstroemeria plant is illustrated by the accompanying photographic drawing in full color showing a blooming umbel of the plant with buds and flowers in different stages of flower development. The color renditions are believed to be as close to the specified color as is possible to obtain by conventional photographic procedures.

DESCRIPTION OF THE NEW PLANT

The following is a detailed description of the new Alstroemeria variety with color designations according to the R.H.S. Colour Chart of The Royal Horticultural Society of London, England. The observations were made on plants grown in a greenhouse in Utah County, Utah, during the summer.

THE PLANT

Origin: Seedling (73-RWR-181A).
Parentage:
*Seed parent.*—Breeding stock plant No. RWR.
*Pollen parent.*—Breeding stock plant No. 181A.
Classification: Alstroemeria hybrid.
Form: Compact, erect bush with a slightly spreading habit having several flower stalks bearing branches with simple umbel arrangement at the tops.
Height: About 35 to 45 cm.

Growth: Erect, vigorous and strong.
Rootstock: Rhizomatous, the rhizomes bear numerous buds which give rise to vegetative and reproductive shoots throughout the growth period. Rhizomes also produce roots, some of which become tuberous.
Foliage:
*Quantity.*—Medium, about 25 to 30 leaves per stem.
*Leaf size.*—About 9.5 cm.
*Leaf shape.*—Elliptical.
*Texture.*—Waxy.
*Color.*—Upper surface — Green. Lower surface — Green.

THE BUD

Form: Pear-shaped. The six petals are perianth and there is no calyx.
Size: Small.
*Diameter.*—8.0 cm.
*Length.*—1.5 cm.
Length of peduncle: 1.5 to 2.0 cm.

THE FLOWER

Blooming habit: Continuous and freely flowering throughout the season.
Flower size: Medium.
*Diameter.*—About 5.0 cm.
*Length.*—About 6.0 cm.
Shape: Generally funnel-like.
Borne: Singly.
Petalage:
*Number.*—Six.
*Arrangement.*—Two concentric circles of three.
*Form.*—Outer petals — Obcordate. Inner petals — Elliptical.
*Texture.*—Smooth.
*Appearance.*—Satiny.
*Color.*—Outer petals: The general color is red-purple. The distal portion is 63C, and the basal part is 63D. There is a darker patch of color, 53B, in the middle of the distal half. Central, on the upper margin is a small green protruberance, 141A. The reverse surface is red-purple, 63C. Three green longitudinal veins originate from the green protruberance and extend over the distal half of the petal through a red colored area, 53B. Inner petals: Upper; The small pointed tip is grey-green. The distal part is red-purple, 63B, and is covered with small purple streaks. The mid section is white with a central yellow-green patch, 1A. The basal part is red-purple, 65B. There are longitudinal streaks of greyed-purple, 187A, covering the basal and mid sections. These streaks are most prominent in the yellow and white areas. The distal portion of the reverse surface is red-purple, 63A with smaller darker streaks visible near the margin. Centrally, there is a yellow-green spot, 1B, below an irregular white band. The basal part is red-purple, 63C. The streaks on the other surface are visible through the petal. Lower; There is a small, pointed, green tip. The general color is red-purple, the distal portion 63A, with small, dark purple streaks, and the basal part, 63C. The two areas of red-purple are separated by a white segment. Longitudinal greyed-purple streaks are prominent across the mid portion. The reverse surface is red-purple, distally 63A, and basally 63C. There is a small white area in the mid section. The streaks on the other surface are visible through the petal.

Persistence: The flowers hang and dry.

Lasting quality: On the plant, 14–18 days.

Main stem or stalk:

*Length.*—40 to 50 cm.

*Color.*—Light green.

*Character.*—Upright, strong and thick.

REPRODUCTIVE ORGANS

Stamens:

*Number.*—Six.

*Arrangement.*—One opposite each petal.

*Anthers.*—Size: 7.0 mm. Color: Green-brown.

*Filaments.*—Length: About 3.5 cm. Color: Pink.

*Pollen.*—Color: Grey-blue.

Pistils:

*Number.*—One.

*Style.*—Length: About 4.0 cm. Color: Pink.

*Stigma.*—Color: Pink.

Fruit:

*Shape.*—Capsular.

*Color.*—Brown at maturity.

What is claimed:

1. A new and distinctive Alstroemeria hybrid, substantially as shown and described herein, characterized by a dwarf habit and large deep pink colored flowers which are borne in attractive inflorscences on relatively dwarf flower stalks.

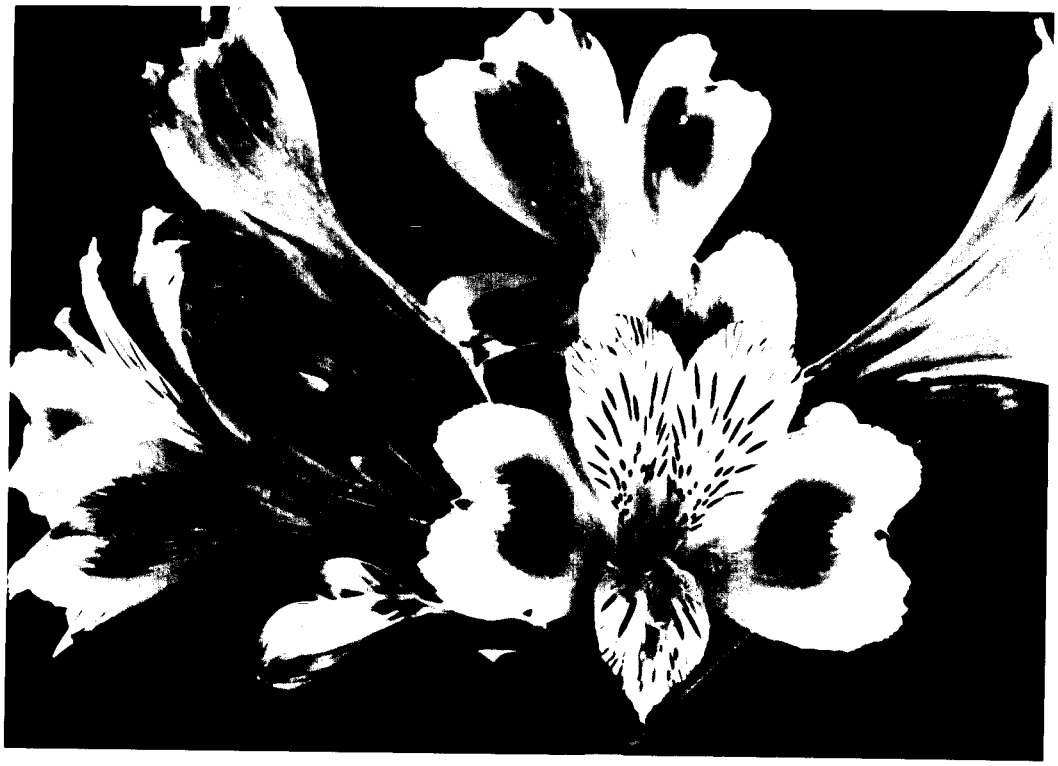

* * * * *